(12) United States Patent
Pashazadeh et al.

(10) Patent No.: US 11,116,994 B2
(45) Date of Patent: Sep. 14, 2021

(54) PATCH WITH ACTIVE INGREDIENTS

(71) Applicants: Ali Pashazadeh, Magdeburg (DE); Nathan Castro, El Paso, TX (US); Dietmar W. Hutmacher, Belbowrie (AU); Michael Friebe, Recklinghausen (DE); Axel Boese, Magdeburg (DE)

(72) Inventors: Ali Pashazadeh, Magdeburg (DE); Nathan Castro, El Paso, TX (US); Dietmar W. Hutmacher, Belbowrie (AU); Michael Friebe, Recklinghausen (DE); Axel Boese, Magdeburg (DE)

( * ) Notice: Subject to any disclaimer, the term of this patent is extended or adjusted under 35 U.S.C. 154(b) by 0 days.

(21) Appl. No.: 16/540,135

(22) Filed: Aug. 14, 2019

(65) Prior Publication Data

US 2020/0054894 A1 Feb. 20, 2020

(30) Foreign Application Priority Data

Aug. 14, 2018 (DE) .................. 10 2018 119 745.4

(51) Int. Cl.
*A61N 5/10* (2006.01)
*A61K 51/12* (2006.01)
*A61N 5/00* (2006.01)

(52) U.S. Cl.
CPC ........ *A61N 5/1029* (2013.01); *A61K 51/1279* (2013.01); *A61N 5/1031* (2013.01); *A61K 51/12* (2013.01); *A61K 2121/00* (2013.01); *A61N 5/00* (2013.01); *G06T 2207/30096* (2013.01)

(58) Field of Classification Search
CPC ...... A61N 5/1029; A61N 5/1031; A61N 5/00; A61K 51/1279; A61K 2121/00; A61K 51/12; G06T 2207/30096
See application file for complete search history.

(56) References Cited

U.S. PATENT DOCUMENTS

| | | | |
|---|---|---|---|
| 2004/0228794 A1* | 11/2004 | Weller | A61K 51/1213 424/1.11 |
| 2015/0202337 A1* | 7/2015 | Di Pasqua | A61K 33/38 424/1.29 |
| 2016/0001094 A1* | 1/2016 | Isham | G01T 1/02 600/1 |
| 2016/0271290 A1 | 9/2016 | Humayun et al. | |

FOREIGN PATENT DOCUMENTS

| | | | | |
|---|---|---|---|---|
| DE | 69614422 | | 5/2002 | |
| EP | 730872 A1 * | | 9/1996 | ......... A61K 51/1279 |
| WO | WO-9921615 A1 * | | 5/1999 | ........... A61N 5/1007 |

(Continued)

OTHER PUBLICATIONS

Shukla, 188Re Tailor Made Skin Patch for the Treatment of Skin Cancers and Keloid: Overview and Technical Considerations, Jul. 31, 2017, International Journal of Nuclear Medicine Research, Special Issue Jul. 2017, 107-113). (Year: 2017).*

(Continued)

*Primary Examiner* — Patrick Fernandes
*Assistant Examiner* — Liam A Wallace

(57) ABSTRACT

The invention relates to a patch (2) with at least one filler and at least one active ingredient, wherein the local distribution of the active ingredient or ingredients within the patch (2) takes place dependent on the morphology, anatomy and physiology of the lesion (1) to be treated.

11 Claims, 1 Drawing Sheet

(56) References Cited

FOREIGN PATENT DOCUMENTS

WO      WO-2012168047 A1 * 12/2012           A61N 5/1029
WO      WO 2015/142316       9/2015

OTHER PUBLICATIONS

Guerra-Rosas, Methodology for diagnosing of skin cancer on images of dermatologic spots by spectral analysis, Sep. 9, 2015, Biomedical Optics Express, vol. 6 No. 10, 3876-3891 (Year: 2015).*
Request for Examination Dated Jan. 18, 2019 from the German Patent and Trademark Office Re. Application No. 10 2018 119 745.4.

* cited by examiner

PATCH WITH ACTIVE INGREDIENTS

RELATED APPLICATION

This application claims the benefit of priority of German Patent Application No. 10 2018 119 745.4 filed on Aug. 14, 2018, the contents of which are all incorporated by reference as if fully set forth herein in their entirety.

FIELD AND BACKGROUND OF THE INVENTION

The invention relates to a therapeutic overlay or a therapeutic implant (referred to as "patch" for short) with active ingredients, and also to a method for producing them.

Skin cancer is the most common type of cancer. Untreated, skin cancer can have serious consequences, possibly including death. In general, surgical removal of the skin tumor is the means of choice. However, there are cases in which surgery is not advisable or is not possible. This is for example the case when the risk of operating is too high for weakened patients, the tumor is located at a site which is difficult to operate on, or when surgical removal is likely to mean major aesthetic restrictions for example on the face.

Known alternatives to surgical removal or to post-operative subsequent treatment of skin cancer are radiation therapies, such as for example external radiation treatment (EBRT—external beam radiation therapy) or brachytherapy. The treatment of other cancerous conditions may also frequently require radiation treatment in addition to surgical or chemotherapeutic measures.

What is disadvantageous about these known internal or external radiation treatments is however the usually high doses of radiation to which the patients are exposed, and that precise use of the radioactive radiation is not always possible. This is still a critical point even with the most up-to-date methods. Although the radiation treatment in the context of the known methods can be applied in a manner which is dosed better and better, the radiation load of the patient is still high, and side-effects in particular due to damage to healthy tissue cannot be completely ruled out. This applies for example for skin cancer in particular when the tumor is in the immediate vicinity of sensitive organs, such as for example the eye, or of sensitive tissue, such as for example bone or cartilage.

The same applies for the administration of other active substances which are frequently administered systemically, and thus do not act solely on the tissue to be treated and may possibly damage healthy tissue.

What would be desirable would be a device for treatment which leads to delivery of radiation and/or active substances which is more targeted overall and thus to a reduced radiation load and loading with active substances, but without in so doing putting at risk the desired success of the therapy.

In the prior art, for example different medical plasters or foils with radionuclides for therapeutic use are proposed for this purpose. Thus DE 696 14 422 T2 for example discloses a radioactive plaster or a radioactive film for direct irradiation and a corresponding production method. The known medical plaster or film comprises a layer with a radionuclide and an adhesive, which are sealed by laminating. The radiation dose of the medical plaster or film can be specified by selection and amount of a suitable nuclide.

A similar solution is proposed by EP 0 463 268 A1, the patch/film described therein also being proposed for internal application as an implant. In order to achieve the radiation dose required for therapy to be successful, in particular the use of a plurality of the individual sealed radioactive films is proposed therein.

What is disadvantageous about the prior art is that although the previously known radioactive plasters and foils in general permit therapy with a radiation dose which is reduced overall compared with other radiation treatments, sufficient adaptation of the device for the purpose of actual individualization to the lesion to be treated is not achieved. Rather, adaptation of the known radioactive plasters and foils amounts to nothing more than adaptation to the contour of the lesion, i.e. its morphology, and/or to the provision of a radiation dose approximately (on average or maximally) required for therapy in the form of a radionuclide matrix homogeneously distributed in the medical plaster or film.

Sufficient individualization of such a device would however only exist if the internal anatomy and physiology of the respective lesion were also taken into account in addition to the morphology. This should be taken into consideration as early as when producing such an individualized radioactive device.

For a lesion is characterized not solely by its morphology, but also by its internal anatomy and physiology. Conventional radioactive devices in the form of medical plasters or foils do not sufficiently take this complexity of the lesion into account. They are rather, if provision is made for this at all, adapted above all to the morphology, i.e. the shape, of the lesion and here in particular to the contour thereof.

The radioactive matrix of known devices is configured homogeneously. Such homogeneous loading with radionuclides and resultant uniform irradiation and radiation dose however does not take account of the complexity of a lesion and has disadvantages.

In order to ensure the therapeutic success of such a homogeneously laden device for all the regions of the lesion, a loading amount with radionuclides would have to be selected which also provides a sufficient radiation dose for those regions of the lesion which have to be treated most intensively with radiation. Accordingly, the selected radiation dose is sufficient for those regions of the lesion which are to be treated most intensively with radiation, but this radiation dose is then too high for the other regions. In these other regions of the lesion which are to be treated with radiation, there is consequently an excessive radiation load, with the risk of known side-effects. If on the other hand a decision is taken to have a loading with radionuclides which is lower overall, there is the risk that the loading no longer guarantees a sufficient radiation dose for all the regions of the lesion, and accordingly prevents therapy from being successful. The same applies to devices which merely provide a homogeneous distribution of other active ingredients.

An improved device for treatment should take into account the complete morphology, anatomy and physiology of the lesion, and in addition to an adapted contour also provide a radiation dose and/or active-substance dose or radionuclide and/or active-substance loading which is adapted for the different partial regions of the lesion.

SUMMARY OF THE INVENTION

It is therefore an object of the invention to make available a patch which, both in its form and in the type, amount and distribution of the active ingredients, such as radioactive nuclides and other active ingredients, can be adapted individually to the lesion to be treated.

Further, the individually adaptable patch should be able to be produced quickly and inexpensively.

This object is achieved by a patch having the features of claim 1 and claim 12, and by a method having the features of claim 8 or 9. Advantageous configurations are in each case the subject of the dependent claims. It should be pointed out that the features listed individually in the claims may also be combined with one another in any technologically sensible manner whatsoever and thus reveal further configurations of the invention.

A lesion within the spirit of the invention is understood to mean any pathological change in human or animal tissue. Such a change may be in the form of benign or malignant tumors, but lesions within the spirit of the invention are not restricted to this. Rather, lesions may also be changes to the tissue caused by infections, inflammation or other pathologies. Frequently, in the present description the treatment of certain conditions such as skin cancer will be discussed by way of example. It is however clear to the person skilled in the art with reference to the described configurations of the patch that treatment of other clinical pictures is also possible with a patch according to the invention, this already being made clear by the preceding definition of the term "lesion".

The term "patch" is used below in unifying manner for highly varied medical devices such as medical plasters, foils, applied layers, implants etc. A patch in this case may comprise any three-dimensional form, i.e. also an amorphous form which does not follow any simple symmetry.

A patch according to the invention may be provided for external application, for example as a medical plaster, or for internal application, for example as an implant.

A patch according to the invention comprises at least one filler and at least one active ingredient. Preferably the fillers and the active ingredients are suitable for processing by a 3D printer.

Fillers within the spirit of the invention are those substances which are suitable for taking up active ingredients in a matrix. In this case, the formulation "taking up in a matrix" is to be understood to mean any form of taking-up. Taken-up active ingredients may correspondingly enter into chemical bonds with the fillers, but also purely physical processes are conceivable, for example in that the fillers form (micro) compartments into which active ingredients, if applicable with further fillers, can be introduced. Such compartments may in this case be produced adapted both in height and also in area to the dimensions necessary for sufficient taking-up of active ingredients.

Combinations of different fillers are conceivable. Thus, for example a first filler may be provided primarily for compartmentalizing the patch, and a second filler primarily for binding the active ingredients. Such a second filler may for example be a superabsorber (SAP=superabsorbent polymers), in order to take up for example liquid active ingredients.

Fillers within the spirit of the invention are furthermore also those substances which ensure the desired mechanical properties of the patch such as rigidity and flexibility, such as for example polymers, hydrogels, gelatin, sugar, etc.

For implantable patches, furthermore those fillers which have biocompatible and if applicable also bioresorbable properties, such as for example known polylactides (for example PLLA), are suitable. Bioresorbable fillers have the advantage that the implant dissolves after a time which can be specified and does not have to be removed by a further operation with its associated risks. The dissolution time depends on the required retention time of the implant. This may be geared for example to the necessary radiation dose or other parameters. By matching the selected active ingredient and the selected bioresorbable filler, the person skilled in the art can set both an optimum fit of the patch and an optimum dissolution rate, and hence irradiation dose or alternatively active-substance delivery.

The person skilled in the art will select the fillers according to the respective requirements.

Active ingredients within the spirit of the invention comprise in particular biologically active substances, which will be divided below in generalized manner into radioactive substances, namely radionuclides, and non-radioactive substances, namely active substances.

Radionuclides within the spirit of the invention are all radionuclides emitting α, β or γ radiation, with radionuclides emitting β radiation such as for example Y-90, P-32 having proved particularly advantageous for most envisaged fields of application owing to their appropriate radiation depth of a few millimeters. The invention is however in no way restricted to the use of these specific β-emitting substances, rather the person skilled in the art will select the radionuclide best suited for the respective treatment according to his judgement.

Further, radionuclides within the spirit of the invention are also those stable nuclides which can be converted into radioactive nuclides only by energy-rich irradiation with neutrons, such as for example Ho-165. The invention is not restricted to the use of Ho-165: many further stable nuclides of this type are known to the person skilled in the art. The selection of a stable nuclide such as Ho-165 is advantageous for the production process, since thus the possible radiation load and the risk of unwanted irradiation for the personnel dealing with production can be minimized.

A suitable radionuclide is selected, taking into account the anatomy and physiology of the lesion. Thus, it is conceivable to equip the patch with the same or with different radionuclides, it being possible to select the radionuclides according to half-life, radiation type and radiant energy. What is advantageous about a patch with different radionuclides is that due to the selection of the radionuclides thereof the radiation dose within the patch can be set precisely to the radiation dose required for the treatment of the individual partial regions of the lesion.

Regions of the lesion which require a higher radiation dose are provided for example with a larger amount of the respective radionuclide or with a radionuclide which is richer in energy. It is also possible to select radionuclides of different radiation types, for example those which emit β radiation, for lesion regions which require a lower radiation dose and lesser radiation depth, and those which emit γ radiation, for lesion regions which require a higher radiation dose and greater radiation depth.

Non-radioactive active substances may for example be antibacterial, antiproliferative or anti-inflammatory active substances. Likewise, it is conceivable to load the patch with adjuvant chemotherapeutics.

The rate of release of the active substances can be made gradual, for example by selecting suitable fillers, which may for example be arranged in several layers and provide a dedicated release matrix by sequential dissolution. Such a patch then comprises multiple layers with fillers of different dissolution rates which release the _g active substances embedded therein accordingly. In particular in the case of implantable patches, gradual release of activate substance is conceivable also by external stimulation.

Further, it is conceivable to load the patch with magnetic particles, which can be activated from the outside for further treatment approaches such as thermal ablation or hyperthermal treatments for generating heat.

Further constituents of the patch can be selected dependent on the respective intended application. Such further constituents may include in particular backing and shielding materials.

Backing materials are in particular those materials which serve for applying a patch. In the case of a patch in the form of a medical plaster, this may for example be an adhesive layer.

Shielding materials within the spirit of the invention are in particular those materials which shield the radioactive radiation emerging from the patch in certain directions and regions. They therefore serve in particular to channel the emitted radiation. Thus, for example in the case of a patch in the form of a medical plaster, the side remote from the contact surface on the skin can be shielded by a corresponding material, so that no radiation can emerge from this side. In the case of implantable patches, for example those regions of the patch which otherwise would emit radiation onto healthy tissue can be shielded by an appropriate material.

To produce a patch according to the invention, first of all a for example digital model of the lesion is created which is based on the data of known imaging methods such as computerized tomography (CT), magnetic resonance imaging (MRT/MRI) or other methods. Such a model can be created for all conceivable lesions. These may be superficial lesions of the skin as well as lesions of the internal organs or bones.

Using the data gathered by the imaging methods and the findings relating to morphology, anatomy and physiology of the lesion obtained by the model, an individualized patch can be produced which in its form, size, if applicable compartmentalization and loading with active ingredients, and also if applicable with further backing and shielding materials, is matched as precisely as possible to the morphology, anatomy and physiology of the lesion.

To this end, the model of the lesion is first of all divided into defined therapeutically sensible partial regions. The lesion is therefore mapped. Therapeutically sensible partial regions in this case are those regions of the lesion which require identical treatment to the greatest possible extent in particular with respect to the necessary radiation dose and if applicable with respect to the type and amount of further active substances. Corresponding indicators may be defined beforehand and permit rapid and optionally also computer-aided division of the lesion into the corresponding partial regions.

The production or loading of the patch then takes place with those active ingredients which are matched to the respective partial regions of the lesion which provide a radiation dose and radiant energy or active-substance dose which is precisely matched for these partial regions.

Furthermore, using the data gathered by the imaging methods, all further substances such as fillers and optionally backing and shielding materials can also be selected specifically for the respective partial regions of the lesion and introduced into the patch.

The person skilled in the art will select the active ingredients and further substances and materials according to the therapy required.

All the constituents of the patch, be they filler materials or backing materials, radionuclides or other active substances, are introduced into the patch in optimized manner, matched to the respective partial region of the lesion. Due to this precise matching of the individual components, a patch which is optimized for the therapy is made available.

A first method for producing a patch according to the invention comprises the following steps:

(A1) creating a digital model of the lesion to be treated using data obtained by means of imaging methods,
(B1) dividing the lesion into partial regions according to definition,
(C1) determining the substances necessary for each partial region of the lesion such as fillers and active ingredients,
(D1) preparing the patch using the substances determined according to step (C1),
(E1) if applicable, activating stable nuclides by energy-rich neutron irradiation.

Optional application of a carrier layer and/or a shielding layer is possible in particular in or after step (D1) but may also take place after step (E1).

A second method for producing a patch according to the invention comprises the following steps:

(A2) creating a digital model of the lesion to be treated using data obtained by means of imaging methods,
(B2) dividing the lesion into partial regions according to definition,
(C2) determining the substances necessary for each partial region of the lesion such as fillers and active ingredients,
(D2) preparing the patch using the fillers determined according to step (C) for creating a compartmentalized patch,
(E2) filling the compartments with the active ingredients and if applicable further fillers determined according to step (C), and
(F2) if applicable, activating stable nuclides by energy-rich neutron irradiation.

Optional application of a carrier layer and/or a shielding layer is possible in particular in or after step (D2) but may also take place in or after step (E2) or (F2).

In a preferred embodiment, the patch according to the invention is produced by means of 3D printing processes. Accordingly, it is conceivable for the data of the lesion to be treated which is obtained by means of imaging methods to be evaluated by a computer using previously generally defined possible degrees of severity of a lesion, and for the lesion to be treated to be divided accordingly into partial regions. This data can then be transmitted to a 3D printer. The software used has available to it definitions of certain compositions of fillers, radionuclides and if applicable further active substances which correspond to the respective degree of severity and can create a patch which is individualized to the lesion to be treated.

Accordingly, the person skilled in the art will select the materials required for producing the patch in the 3D printing process such as for example fillers, active ingredients such as radionuclides and active substances etc. according to whether they are suitable for such a 3D printing process. In this case, embodiments in which all the parts of the patch are produced by means of 3D printing processes are conceivable, but embodiments in which only certain parts of the patch or certain steps of the methods previously described or only certain partial steps of the methods previously described are created by means of 3D printing processes are also conceivable.

Thus in addition to the production of the patch according to the invention in a 3D printing process, which production is to the greatest possible extent complete, in particular also those methods in which for example step (D1) of the first method described or steps (D2) and (E2) of the second method described are produced by means of 3D printing processes, but the attachment of the backing and shielding layer takes place with other means, are conceivable. It is also conceivable for step (D2) of the second method described to be carried out by means of 3D printing processes, but for the introduction of the active ingredients according to step (E2) to take place entirely or partly with other means, for example by manual introduction of the active ingredients. The person skilled in the art here will select the best combination according to the problem posed.

The carrier layer and/or the shielding layer may also optionally be produced by means of 3D printing. In this case it is conceivable for them to be produced separately in a first step, and then to be fixed to the rest of the patch in a further step: it is however also conceivable for the patch including the carrier layer and/or the shielding layer to be prepared in one piece by means of 3D printing.

What is advantageous about a one-piece method is the possibility of complete automation in a 3D printing process.

A 3D printing process overall has the advantage that the materials used for producing the patch can be introduced into the patch in automated manner in a very precise dose and with very precise localization. Accordingly, computer-aided production of a patch in which the loading with the substances required can take place as precisely as possible at the radiation dose and/or active-substance dose necessary for the therapy is possible. Corresponding regions of the patch which deliver an increased radiation dose lie against regions of the lesion which require a higher radiation dose. Regions of the patch which deliver a lower radiation dose lie against regions of the lesion which require a lower radiation dose. The same applies analogously to the further active substances.

The fillers forming the matrix in this preferred 3D printing process can also be introduced into the patch extremely precisely. Thus, patches for implantation which for example dissolve gradually and thus release the various active substances introduced in a therapeutically sensible sequence are conceivable. Such an implant may be constructed for example from various layers. The alternative or additionally possible compartmentalization makes the patch according to the invention still more flexible.

Thus, in particular also those embodiments are conceivable in which first of all a patch without active ingredients is produced, the compartmentalization being adapted as precisely as possible to the morphology, anatomy and physiology of the lesion. Above all in the event that the active ingredients to be introduced into the compartments are not or only limitedly storable or are not suited for 3D printing, the prepared patch can quickly be loaded with these substances and then applied. Thus, for example in the case of liquid active ingredients one compartment may be equipped with an absorbent further filler, for example with a superabsorber, which is then laden with the liquid active ingredient.

The areas of application of a patch according to the invention are many and diverse, and as described are not limited to the treatment of skin tumors or other external applications, but rather are also suitable as implants. When implanted, the patches can be used for example for subsequent treatment of surgical sites of removed tumors, in order for example to subsequently treat remnants of lesions which still remain by radiation treatment or chemotherapeutics or other active ingredients, or alternatively to improve wound healing by using other active substances such as anti-inflammatories or antibiotics. In this connection, implantable patches, which as a further function serve as a framework for re-growing healthy cells, are also conceivable.

Such an implant may for example comprise a further layer which dissolves more slowly than the other layers of the implant and thus serves as a growth framework once for example the layers with active ingredients have already dissolved.

The production of a patch according to the invention with 3D printing processes also permits the provision of complex forms, such as for example lattice structures or tubes. Thus, patches can be provided for body cavities such as tracheas or oesophagi or alternatively blood vessels as well.

Thus, patches according to the invention are also suitable for the aftercare of angioplasty procedures such as vasodilation in addition to the treatment of tumors.

Such procedures always hold the risk of renewed vasoconstriction due to uncontrolled cell growth at the treatment site, which can be reduced by the introduction of radionuclides or alternatively of antiproliferative medicaments.

The patch according to the invention has the advantage over the prior art that very precise distribution of the active ingredients used is possible. Thus, the radiation dose and/or active-substance dose to be delivered can be matched exactly to the morphology, anatomy and physiology of the lesion to be treated. As a result, both excessively high doses which might damage healthy areas of tissue and excessively low doses which do not achieve a sufficient therapeutic effect are avoided.

One further advantage of the patch according to the invention consists in that the three-dimensional form can be adapted very precisely to the shape of the treatment site. This relates to external application just as much as to internal application. Thus, for example in the case of an implant the form of the patch including the backing and/or shielding layers can be adapted very precisely to the shape of the tissue or structure to be treated. In the case of a patch which is to be used externally as a medical plaster, the form can for example be adapted precisely to the contour of the skin surface. This accuracy of fit increases the irradiation accuracy within the lesion and at the same time minimizes the effect of radiation and active substances in healthy tissue. Not least, one significant advantage of the patch according to the invention lies in the production which despite individualization is simple and, due to the use of 3D printing processes, inexpensive and rapid.

The invention and its technical context will be discussed in greater detail below with reference to the figures. It should be pointed out that the figures show a particularly preferred variant embodiment of the invention. The invention is however not restricted to the variant embodiment shown. In particular, the invention, in so far as it is technically sensible, covers any combinations whatsoever of the technical features which are outlined in the claims or are described in the description as being relevant to the invention.

DESCRIPTION OF SPECIFIC EMBODIMENTS OF THE INVENTION

Figure 1A:
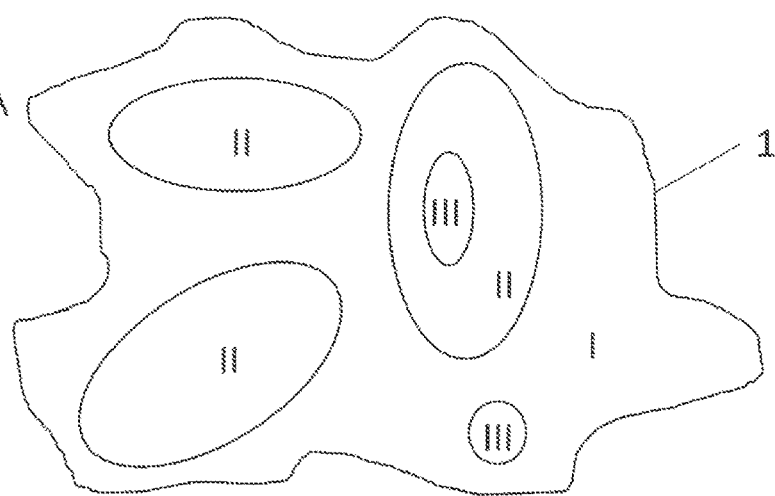
FIG. 1A is a diagrammatic representation of a lesion divided into varying partial regions.

FIG. 1A shows a diagrammatic two-dimensional view of a lesion 1, for example a skin tumor. Such a model of the lesion to be treated is based for example on data obtained by means of imaging methods. This data is suitable also for creating a three-dimensional model, which will not be discussed at this point solely for reasons of clarity.

The model of the lesion is divided into partial regions. This can be done solely by the assessment of a person skilled in the art or alternatively with the aid of a computer. The regions thus defined correspond for example to a previously defined severity of the respective disease, for example a particular tumor stage, a particular cell density, etc., as made clear by the Roman numerals I to III, and require individual treatment in each case. The differentiation may understandably comprise substantially more degrees than only the I to III shown by way of example.

In the present case, the lesion 1 has been divided into six partial regions, of which one partial region corresponds to definition I, three partial regions to definition II and two partial regions to definition III.

Figure 1B:
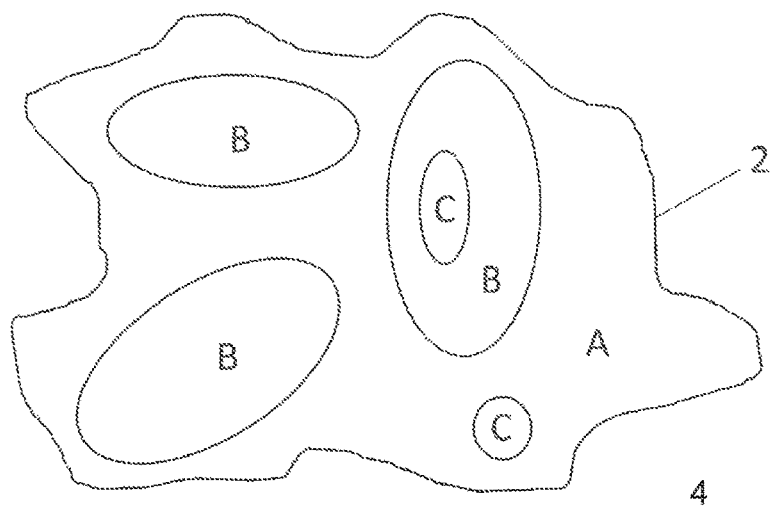
FIG. 1B is a diagrammatic representation of the patch manufactured for the lesion of FIG. 1A.

FIG. 1B shows a patch 2 prepared for the lesion 1 according to FIG. 1A. The patch 2 contains, for each of the partial regions of the lesion, a specific loading with active ingredients which are matched in each case precisely to the necessary treatment of the respective partial region and are designated A, B and C. The differentiation may of course comprise substantially more treatment possibilities than the A, B and C shown by way of example. Alternatively, it is conceivable for the patch initially to comprise solely the fillers and to be divided into the compartments A, B and C, which are only laden with the active ingredients provided in each case in a further step.

Preferably such a patch 2 is produced by means of 3D printing processes. Accordingly, it is conceivable that the data obtained by means of imaging methods is evaluated by a computer using the previously defined degrees of severity of the lesion (here I to III), and this data is then transmitted to a 3D printer. A 3D printer programmed with correspondingly defined treatments (here A to C) and provided with corresponding substances will then be able to print a corresponding patch.

Figure 1C:
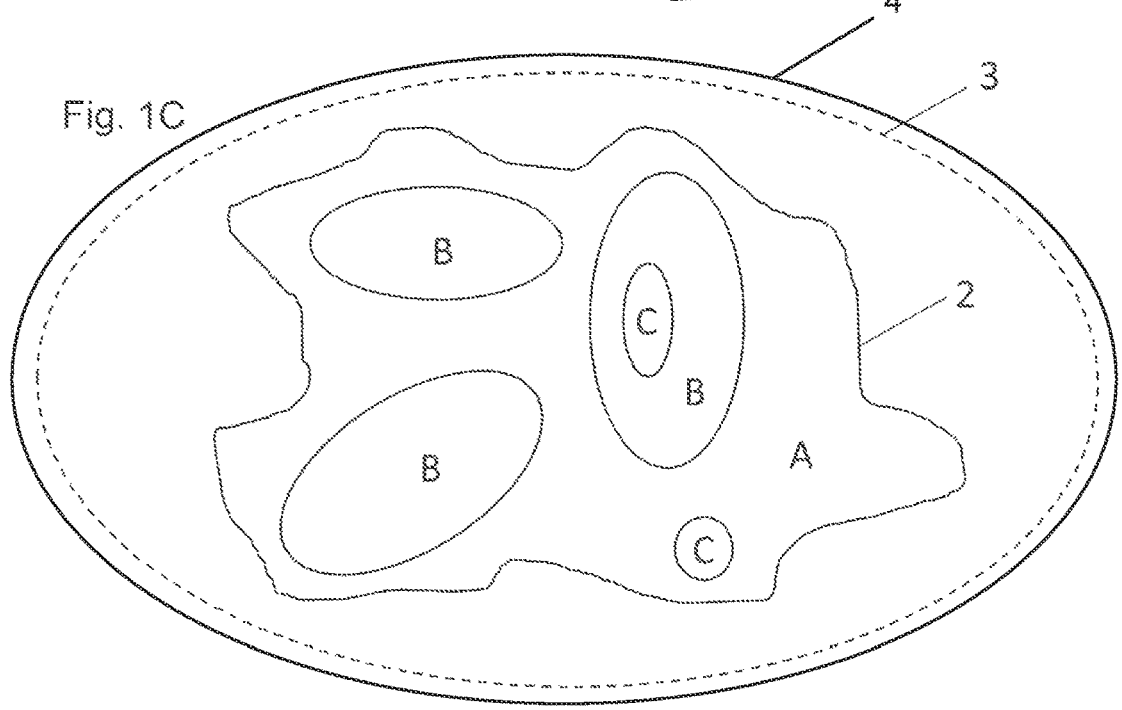
FIG. 1C is a diagrammatic view of the patch of FIG. 1B with a further backing material.

FIG. 1C shows the patch 2 of FIG. 1B, with a carrier layer 3 having been applied on or if applicable also around the patch 2. Thus, the patch 2 can be applied for example as a medical plaster. A shielding layer can be provided as a further layer (not shown).

LIST OF REFERENCE CHARACTERS 1 lesion
2 patch
3 backing material
I-III defined degrees of severity
A-C defined loading

What is claimed is:

1. A patch with a plurality of fillers and at least one active ingredient, wherein a local distribution of the at least one active ingredient within the patch (2) takes place dependent on a morphology, anatomy and physiology of a lesion (1) to be treated; and
   wherein the patch comprises the plurality of fillers contained in a plurality of compartmentscontainingtheatleastoneactiveingredientandformedinthepatchtocovera plurality of different regions of the lesion (1);
   wherein at least one of the plurality of fillers having multiple layers to devise a different dissolution rate from other fillers of the plurality of fillers.

2. A patch according to claim 1 wherein at least one of the plurality of compartments having a different active ingredient from the other compartments of the plurality of compartments.

3. The patch according to claim 1, wherein the patch (2) comprises at least one backing material (3).

4. The patch according to claim 1, wherein the patch (2) comprises at least one shielding material.

5. The patch according to claim 1, wherein the at least one active ingredient comprises a radionuclide or an active substance, the radionuclide being selected from radionuclides emitting $\alpha$-, $\beta$- or $\gamma$-radiation and/or from stable nuclides.

6. A method for producing a patch (2) according to claim 1, comprising the following steps:
   (A1) creating a digital model of the lesion (1) to be treated using data obtained by means of imaging methods,
   (B1) dividing the lesion (1) into partial regions according to definition,
   (C1) determining at least one substance necessary for each partial region of the lesion (1) such as at least one of the plurality of fillers and at least one active ingredient,
   (D1) preparing the patch (2) using the at least one substance determined according to step (C1),
   (E1) if applicable, activating stable nuclides by energy-rich neutron irradiation.

7. The method for producing a patch (2) according to claim 6, wherein at least the preparation of the patch (2) according to step (D1) takes place by a 3D printing process.

8. Method for producing a patch (2) according to claim 1, comprising the following steps:
   (A2) creating a digital model of the lesion (1) to be treated using data obtained by means of imaging methods,
   (B2) dividing the lesion (1) into partial regions according to definition,
   (C2) determining at least one substance necessary for each partial region of the lesion (1) such as at least one of the plurality of fillers and at least one active ingredient,
   (D2) preparing the patch (2) using the at least one of the plurality of fillers determined according to step (C2) for creating a compartmentalized patch (2), and
   (E2) filling at least one compartment of the compartmentalized patch (2) with the at least one active ingredient and if applicable further of the at least one of the plurality of fillers determined according to step (C),
   (F2) if applicable, activating stable nuclides by energy-rich neutron irradiation.

9. A method for producing a patch (2) according to claim 6, wherein after step (D) or (step (E1), in a further step (D1') or (E1') respectively, a further backing material (3) and/or shielding layer is applied.

10. A method for producing a patch (2) according to claim 9, wherein after step (D2), step (E2) or step (F2), in a further step (D2'), (E2') or (F2') respectively, a further backing material (3) and/or shielding layer is applied.

11. A method for producing a patch (2) according to claim 9, wherein at least the preparation of the patch (2) according to step (D2) takes place by a 3D printing process.

* * * * *